United States Patent
Gaspar et al.

(10) Patent No.: US 9,382,397 B2
(45) Date of Patent: *Jul. 5, 2016

(54) BLOWING CATALYST

(75) Inventors: Zsolt Gaspar, Petfurdo (HU); Heiko Heinrich Humbert, Hamburg (DE); Gabor Felber, Veszprem (HU); Attila Gaspar, Petfurdo (HU); Robert Allison Grigsby, Jr., Spring, TX (US); Imre Kordas, Veszprem (HU); Petra Emma Vanderstraeten, Leuven (BE)

(73) Assignees: Huntsman Corporation Hungary Zrt, Petfurdo (HU); Huntsman International LLC, The Woodlands, TX (US)

( * ) Notice: Subject to any disclaimer, the term of this patent is extended or adjusted under 35 U.S.C. 154(b) by 277 days.

This patent is subject to a terminal disclaimer.

(21) Appl. No.: 13/990,070

(22) PCT Filed: Nov. 22, 2011

(86) PCT No.: PCT/EP2011/070611
§ 371 (c)(1),
(2), (4) Date: May 29, 2013

(87) PCT Pub. No.: WO2012/072441
PCT Pub. Date: Jun. 7, 2012

(65) Prior Publication Data
US 2013/0261199 A1 Oct. 3, 2013

Related U.S. Application Data

(60) Provisional application No. 61/417,551, filed on Nov. 29, 2010.

(30) Foreign Application Priority Data

Jan. 7, 2011 (EP) ..................... 11462001

(51) Int. Cl.
*C07C 217/42* (2006.01)
*C08J 9/04* (2006.01)
*C07C 217/08* (2006.01)
*C08G 18/18* (2006.01)
*C08G 18/66* (2006.01)
*C08G 101/00* (2006.01)

(52) U.S. Cl.
CPC ................ *C08J 9/04* (2013.01); *C07C 217/08* (2013.01); *C07C 217/42* (2013.01); *C08G 18/1825* (2013.01); *C08G 18/1833* (2013.01); *C08G 18/1841* (2013.01); *C08G 18/6688* (2013.01); *C08G 2101/005* (2013.01); *C08G 2101/0008* (2013.01); *C08G 2101/0083* (2013.01); *C08G 2290/00* (2013.01)

(58) Field of Classification Search
CPC ............................ C07C 217/42; C07C 217/08
See application file for complete search history.

(56) References Cited

U.S. PATENT DOCUMENTS

| | | | |
|---|---|---|---|
| 5,213,584 A | 5/1993 | Izaiku et al. | |
| 5,756,558 A * | 5/1998 | Savoca ................ | C07C 217/088 521/115 |
| 6,759,447 B1 * | 7/2004 | Burdeniuc ......... | C08G 18/1841 521/128 |
| 7,872,055 B2 | 1/2011 | Burdeniuc et al. | |
| 8,664,445 B2 * | 3/2014 | Gaspar .................. | C07C 213/02 564/474 |
| 8,822,729 B2 * | 9/2014 | Gaspar .................. | C07C 213/02 252/182.23 |
| 2008/0293841 A1 * | 11/2008 | Andrew ............... | C08G 18/161 521/157 |
| 2011/0009512 A1 | 1/2011 | Grigsby, Jr. et al. | |
| 2012/0071622 A1 | 3/2012 | Gaspar et al. | |
| 2012/0130132 A1 | 5/2012 | Humbert et al. | |

FOREIGN PATENT DOCUMENTS

| DE | 848825 C | 9/1952 |
|---|---|---|
| DE | 2618280 A | 11/1977 |
| EP | 2196493 A | 6/2010 |
| WO | 2009/117479 A | 9/2009 |

* cited by examiner

*Primary Examiner* — John Cooney
(74) *Attorney, Agent, or Firm* — Huntsman International LLC

(57) ABSTRACT

The invention relates to a primary amine component corresponding to formula I being $(R^1R^2NR^3)_2NR^4$ wherein
each of $R^1$ and $R^2$ are chosen from the group consisting of a methyl group, an ethyl group, an iso-propyl group and an n-propyl group;
$R^3$ being an alkoxyalkyl group chosen from the group consisting of —$CH_2CH_2OCH_2CH_2$—, —$CH_2CH_2OCH_2CH_2CH_2$— and —$CH_2CH_2CH_2OCH_2CH_2CH_2$—;
$R^4$ is chosen from the group consisting of a hydrogen and —$CH_2CH_2NH_2$,
and the use of said primary amine component corresponding to Formula I as a blowing catalyst of a catalyst system in a reaction of at least one polyisocyanate component and at least one isocyanate-reactive component, the catalyst system further comprising at least one gelling catalyst different from said component of formula I.

6 Claims, No Drawings

BLOWING CATALYST

This application is the National Phase of International Application PCT/EP2011/070611 filed Nov. 22, 2011 which designated the U.S. and which claims priority to E.P. Application Serial No. 11462001.6 filed Jan. 7, 2011 and U.S. Application Ser. No. 61/417,551 filed Nov. 29, 2010. The noted applications are incorporated herein by reference.

The present invention relates to catalyst systems for polyurethane and/or polyurea foam production, and blowing catalysts of such catalyst system.

Polyurethane and polyurea products, and in particular foamed polyurethane products, are well known in the art and used for a multitude of different applications.

The foamed polyurethane products (hereinafter referred to as foamed PU), are obtained by reacting a polyisocyanate with a isocyanate reactive component, typically a polyalcohol (also called polyol).

The reaction to provide the foamed PU typically requires a catalyst system comprising at least two catalyst components. The first component is typically referred to as the gelling catalyst or gelation catalyst, mainly catalyzing the reaction of isocyanate groups and alcohol groups, thereby providing urethane groups in the polyurethane polymer obtained. The second component is typically referred to as the blowing catalyst, mainly catalyzing the reaction of isocyanate groups and water, thereby providing urea groups in the polyurethane polymer obtained and carbon dioxide gas.

Additional additives such as chain extenders, other chemical or physical blowing agents, fillers, flame retarders, antioxidants and alike can be added.

Typically the catalyst system is to meet various criteria to a more or less extent, in order to be a suitable catalyst system for the foamed PU aimed for. Such criteria is a.o. the catalytic activity of the gelling catalyst, which typically is to be as high as possible, causing less catalyst to be used in order to obtain the proper reaction rate and obtaining a quick start of the reaction. An other criteria is a.o. the catalytic activity of the blowing catalyst, which typically is to be high in order to cause less catalyst to be used, but which may not be too high, as this might cause the developing foam to collapse due to the provision of too much gas in the reacting system. A blowing catalyst which has a constant catalytic activity during the whole reaction time of the foam may be desired. Other criteria of the catalytic system may be the release of low or even no VOC's from the manufactured foam. Still an other criteria of the catalytic system may be the provision of a foam showing less or no tendency to fogging.

Preferably the catalytic system is able to react different polyisocyanates with different isocyanate reactive components is a similar or even identical way.

A catalyst with formula $(R^1R^2NR^3)_3N$ or $(R^1R^2NR^3)_2NCH_3$, wherein each of $R^1$ and $R^2$ are a methyl group, and $R^3$—$CH_2CH_2OCH_2CH_2$— is known from DE2618280.

Surprisingly we found several components that are suitable as blowing catalyst of a catalyst system for use in polyurethane and/or polyurea foam providing reactions, which blowing catalysts meet one or more of the criteria as set out above.

According to a first aspect of the present invention, the use is provided of a component according to one of the formula I, formula I being $(R^1R^2NR^3)_2NR^4$, wherein each of $R^1$ and $R^2$ are chosen from the group consisting of a methyl group, an ethyl group, an iso-propyl group and an n-propyl group;

$R^3$ being an alkoxyalkyl group chosen from the group consisting of —$CH_2CH_2OCH_2CH_2$—, —$CH_2CH_2OCH_2CH_2CH_2$— and —$CH_2CH_2CH_2OCH_2CH_2CH_2$—;

$R^4$ is chosen from the group consisting of a hydrogen and —$CH_2CH_2CH_2NH_2$, as a blowing catalyst of a catalyst system in a reaction of at least one polyisocyanate component and at least one isocyanate-reactive component, the catalyst system further comprising at least one gelling catalyst different from said component of formula I.

Hence it functions as the blowing catalyst in a reactive system of, on the one hand, at least one, but optionally more than one polyisocyanate component, and on the other hand the combination of the at least one, and possibly more than one, isocyanate-reactive component and all other components other than the isocyanates in the reaction system, such as, as the case may be, the polyol, water, any additives such as surfactants, flame retardants, antioxidants, and amine catalysts.

The component according to the formula I can be provided, in general, by a method for providing a secondary or tertiary amine with formula $(R^1R^2NR^3)_2NR^4$, wherein each of $R^1$ and $R^2$ are chosen from the group consisting of a methyl group, an ethyl group, an iso-propyl group and an n-propyl group;

$R^3$ being an alkoxyalkyl group chosen from the group consisting of —$CH_2CH_2OCH_2CH_2$—, —$CH_2CH_2OCH_2CH_2CH_2$— and —$CH_2CH_2CH_2OCH_2CH_2CH_2$—;

$R^{4'}$ is chosen from the group consisting of a hydrogen, a methyl group, an ethyl group, an iso-propyl group, an n-propyl group and a group with formula $R^1R^2NR^3$, the method comprising the steps:

(α) reacting $R^1R^2NR^3(OH)$ with ammonia, thereby providing a mixture comprising $(R^1R^2NR^3)_2NR^{4'}$;

(β) separating $(R^1R^2NR^3)_2NR^{4'}$ from said mixture.

It was found that the reaction of ammonia with the $R^1R^2NR^3(OH)$, preferably in presence of a catalyst, provides mixtures of components, which mixtures comprise, next to the corresponding $(R^1R^2NR^3)_2NH$, at least one of a corresponding primary amine $R^1R^2NR^3NH_2$, a secondary amine $R^1R^2NR^3NR^5H$, and/or a tertiary amine $R^1R^2NR^3NR^5R^6$, wherein $R^5$ and optionally $R^6$ are identical to $R^1$ or $R^2$. Further, it was noticed that also other amines, with general formula $(R^1R^2NR^3)_2NR^{4'}$ may be obtained, for which $R^{4'}$ equals either $R^1$, $R^2$ or $(R^1R^2NR^3)$.

Without wishing to be bound by any theory, it is believed that these latter amines are provided by trans-alkylation of the alkyl groups on the amines.

As an example, in case of an alkanol with formula $R^1R^2NR^3(OH)$ wherein each of W and $R^2$ are a methyl group, and wherein $R^3$ being an alkoxyalkyl group chosen from the group consisting of —$CH_2CH_2OCH_2CH_2$—, —$CH_2CH_2OCH_2CH_2CH_2$— and —$CH_2CH_2CH_2OCH_2CH_2CH_2$—, a mixture comprising an amine with formula $((CH_3)_2NR^3)_2NH$, and further comprising a primary amine of the general formula $(CH_3)_2NR^3NH_2$, a secondary amine of formula $(CH_3)_2NR^3NH(CH_3)$ and a tertiary amine with formula $(CH_3)_2NR^3N(CH_3)_2$ may be obtained. Also present in this mixture are components with formula $((CH_3)_2NR^3)_3N$, next to $((CH_3)_2NR^3)_2NCH_3$.

The $R^1R^2NR^3(OH)$ may be reacted with ammonia in presence of a catalyst. So-called copper-chromite catalysts are examples of typical oxidic catalysts of Group I B/VI B of Periodic Table of elements, which catalysts are suitable for the reaction of N,N-2-dialkylaminoalkoxyalkanol with ammonia.

Numerous promoters may be used, mainly comprising elements of the Groups I A and II A, IV B, IV A, VIII B. Other suitable catalysts for alcohol amination reaction are supported or non-supported catalysts of the Group of VIII B. Carriers for group VIII B metals are $Al_2O_3$, $SiO_2$, $TiO_2$, activated carbon, etc. Also, it is popular to add different promoters to such catalyst, mainly of the Groups I A and II A, IV B, IV A.

Carriers like $Al_2O_3$, $SiO_2$, $TiO_2$ may show appreciable activity for alcohol amination reactions. Promoters can be added, which are covering a wide range of components.

The separation of $(R^1R^2NR^3)_2NR^{4'}$ from the mixture may typically be done by distillation.

The distillation provides different fractions, of which typically the heavy fraction comprises $((R^1R^2NR^3)_2NR^{4'}$, together with isomers of this molecule. Typically, in case of an amine with formula $(R^1R^2NR^3)_2NH$ wherein each of $R^1$ and $R^2$ are chosen from the group consisting of a methyl group, an ethyl group, an iso-propyl group or an n-propyl group;

$R^3$ being an alkoxyalkyl group chosen from the group consisting of —CH2CH2OCH2CH2—, —$CH_2CH_2OCH_2CH_2CH_2$— and —$CH_2CH_2CH_2OCH_2CH_2CH_2$—, the heavy fraction comprises $(R^1R^2NR^3)_2NH$, together with corresponding transalkylated amines with general formula $(R^1R^2NR^3)_2NR^{4'}$ for which $R^{4'}$ equals either $R^1$, $R^2$ or $(R^1R^2NR^3)$.

In case of bis-(N,N-2-dimethylamino-ethoxy-ethyl)-amine, the following compounds, additional to the primary amine of the general formula $(CH_3)_2NR^3NH_2$, the secondary amine of formula $(CH_3)_2NR^3NH(CH_3)$ and the tertiary amine with formula $(CH_3)_2NR^3N(CH_3)_2$, were found in the mixture obtained by reacting N,N-2-dimethylamino-ethoxy-ethanol with ammonia:

bis(N,N-2-dimethylaminoethoxyethyl)amine

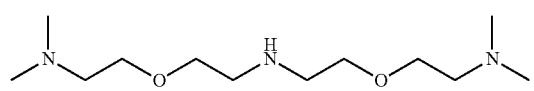

bis(N,N-2-dimethylaminoethoxyethyl)methylamine:

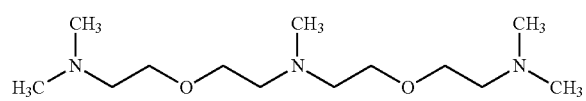

[2-(2-Dimethylamino-ethoxy)-ethyl]-[2-(2-methylamino-ethoxy)-ethyl]-amine or by IUPAC nomenclature: 2,8,14-triaza-5,11-dioxa-2-methyl-pentadecane:

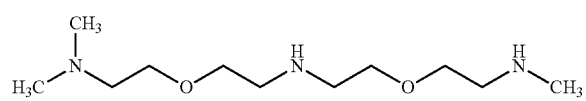

[2-(2-Amino-ethoxy)-ethyl]-[2-(2-dimethylamino-ethoxy)-ethyl]-methyl-amine or by IUPAC nomenclature: 2,8,14-triaza-5,11-dioxa-2,8-dimethyl-tetradecane:

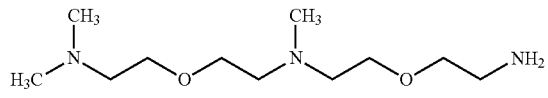

and [2-(2-{Bis-[2-(2-dimethylamino-ethoxy)-ethyl]-amino}-ethoxy)-ethyl]-dimethyl-amine, (also referred to as TM33); MW 362,

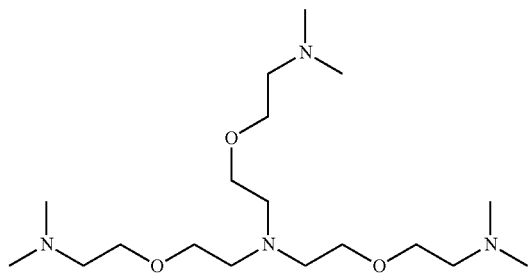

Identification was done using by GC/MS- and NMR spectroscopy.

In order to separate $(R^1R^2NR^3)_2NH$ from $(R^1R^2NR^3)_2NR^{4'}$, $R^{4'}$ equaling either $R^1$ or $R^2$ or $(R^1R^2NR^3)$ can be done by first reacting the mixture of $(R^1R^2NR^3)_2NH$ and $(R^1R^2NR^3)_2NR^{4'}$, with formic acid HCOOH. Only $(R^1R^2NR^3)_2NH$ will undergo a formylation reaction, i.e. react with the formic acid, providing $(R^1R^2NR^3)_2NCOH$. This $(R^1R^2NR^3)_2NCOH$ can be separated from $(R^1R^2NR^3)_2NR^{4'}$ by distillation. The obtained $(R^1R^2NR^3)_2NCOH$ can thereafter be deformylated in alkalinic medium, e.g. in the presence of KOH, providing $(R^1R^2NR^3)_2NH$ and HCOOK.

As such $(R^1R^2NR^3)_2NH$ on the one hand, and $(R^1R^2NR^3)_2NR^{4'}$, $R^{4'}$ equaling either $R^1$ or $R^2$ or $(R^1R^2NR^3)$ on the other hand may be obtained.

The $(R^1R^2NR^3)_2NH$ can be used as blowing catalyst as set out above, i.e. a product with formula $(R^1R^2NR^3)_2NR^4$, $R^4$ being hydrogen.

In the alternative, the tertiary amine with formula $(R^1R^2NR^3)_2NR^4$, wherein $R^4$ is —$CH_2CH_2CH_2NH_2$ can be obtained by first providing $(R^1R^2NR^3)_2NH$ as set out above, and thereafter converting this $(R^1R^2NR^3)_2NH$ into $(R^1R^2NR^3)_2NR^4$ by reacting $(R^1R^2NR^3)_2NH$ with acrilonitrile ($R^4$ being —$CH_2CH_2CH_2NH_2$).

According to some embodiments, the reaction of at least one polyisocyanate component and at least one isocyanate-reactive component may be carried out in presence of water.

According to some embodiments, the component may be a component according to formula I, $R^4$ being hydrogen.

According to some embodiments, $R^1$ and $R^2$ may be methyl

According to some embodiments, the component may be a component according to formula I, $R^4$ being —$CH_2CH_2CH_2NH_2$.

According to some embodiments, the at least one isocyanate-reactive component may be a polyamine.

By means of this use, a polyurea foam is provided.

Typical polyamines are e.g. amine terminated ethylene oxide and/or propylene oxide polymers, having two or more amine groups at the end of the polymer chain. Examples are the JEFFAMINE® polyoxyalkyleneamines of Huntsman International LLC.

According to some embodiments, the at least one isocyanate-reactive component may be a polyol.

By means of this use, a polyurethane foam is provided.

As good as any polyalcohol can be used. Typically polyether polyols or polyester polyols are used.

Given as examples of the polyether polyols are polyethylene glycol, polypropylene glycol, polypropylene glycol-ethylene glycol copolymer, polytetramethylene glycol, polyhexamethylene glycol, polyheptamethylene glycol, polydecamethylene glycol, and polyether polyols obtained by ring-opening copolymerisation of alkylene oxides, such as ethylene oxide and/or propylene oxide, with isocyanate-reactive initiators of functionality 2 to 8. The functionality of the isocyanate-reactive initiators is to be understood as the number of isocyanate-reactive hydrogen atoms per molecule initiator.

Polyester diols obtained by reacting a polyhydric alcohol and a polybasic acid are given as examples of the polyester polyols. As examples of the polyhydric alcohol, ethylene glycol, polyethylene glycol, tetramethylene glycol, polytetramethylene glycol, 1,6-hexanediol, 3-methyl-1,5-pentanediol, 1,9-nonanediol, 2-methyl-1,8-octanediol, and the like can be given. As examples of the polybasic acid, phthalic acid, dimer acid, isophthalic acid, terephthalic acid, maleic acid, fumaric acid, adipic acid, sebacic acid, and the like can be given.

According to some embodiments, a polyurethane rigid foam may be provided

According to some embodiments, a polyurethane semi-rigid foam may be provided.

According to some embodiments, a polyurethane flexible foam may be provided.

According to some embodiments, the at least polyisocyanate component may be toluenediisocyanate (TDI) or diphenylmethane diisocyanate (MDI)-type polyisocyanate.

Suitable polyisocyanate compounds may comprise any number of polyisocyanates, including but not limited to, toluene diisocyanates (TDI), diphenylmethane diisocyanate (MDI)-type polyisocyanates, and prepolymers of these isocyanates, aliphatic isocyanates such as IPDI (isophoronediisocyanate), and hexamethylene diisocyanate and derivatives thereof.

In case diphenylmethane diisocyanate (also known as methylene diphenyl diisocyanate, and referred to as MDI) is used, the diphenylmethane diisocyanate (MDI) can be in the form of its 2,4'-, 2,2'- and 4,4'-isomers and mixtures thereof, the mixtures of diphenylmethane diisocyanates (MDI) and oligomers thereof known in the art as "crude" or polymeric MDI (polymethylene polyphenylene polyisocyanates) having an isocyanate functionality of greater than 2, or any of their derivatives having a urethane, isocyanurate, allophonate, biuret, uretonimine, uretdione and/or iminooxadiazinedione groups and mixtures of the same.

Examples of other suitable polyisocyanates are tolylene diisocyanate (also known as toluene diisocyanate, and referred to as TDI), such as 2,4 TDI and 2,6 TDI in any suitable isomer mixture, hexamethylene diisocyanate (HMDI or HDI), isophorone diisocyanate (IPDI), butylene diisocyanate, trimethylhexamethylene diisocyanate, di(isocyanatocyclohexyl)methane, e.g. 4,4'-diisocyanatodicyclohexylmethane ($H_{12}$MDI), isocyanatomethyl-1,8-octane diisocyanate and tetramethylxylene diisocyanate (TMXDI), 1,5-naphtalenediisocyanate (NDI), p-phenylenediisocyanate (PPDI), 1,4-cyclohexanediisocyanate (CDI), tolidine diisocyanate (TODI), any suitable mixture of these polyisocyanates, and any suitable mixture of one or more of these polyisocyanates with MDI in the form of its 2,4'-, 2,2'- and 4,4'-isomers and mixtures thereof, the mixtures of diphenylmethane diisocyanates (MDI) and oligomers thereof.

Preferred polyisocyanate compounds used for the present invention are polymeric or prepolymeric polyisocyanates, such a quasi-prepolymers, semi-prepolymers or full prepolymers, which may be obtained by reacting polyisocyanates, e.g. polyisocyanates as set out above, and preferably MDI-based polyisocyanates, with compounds containing isocyanate-reactive hydrogen atoms, typically polyamines or polyols.

In the use according to the invention, other additional catalytic components may be used.

Typically, when a polyurethane foamed material is to be provided, also a so-called gelling or gelating catalyst is added to catalyze the isocyanate-alcohol reaction. Typical catalysts are e.g. N-(3-dimethylaminopropyl)-N,N-diisopropanolamine (DPA), triethylenediamine (available from Huntsman as Jeffcat® TD-catalysts), N,N,N',N'',N-pentamethyldipropylenetriamine, N,N,N-tris-(3-dimethylaminopropyl-)amine, N-(3-dimethylaminopropyl)-N,N-diisopropanolamine, N'-(3-(dimethylaminopropyl)-N,N-dimethyl-1,3-propanediamine, Jeffcat® LE-310, Jeffcat® Z-131, or combinations thereof.

Also additional blowing catalysts may be added, such as e.g. 2,2-dimorpholinodiethylether, N,N,N'-trimethyl-N'-hydroxyethyl-bisaminoethylether, bis(2-dimethylaminoethyl) ether (available from Huntsman as Jeffcat® ZF catalysts), or combinations thereof.

According to some embodiments, the component may be a component according to formula I,
each of $R^1$ and $R^2$ are a methyl group;
$R^3$ being —$CH_2CH_2OCH_2CH_2$—;
$R^4$ is hydrogen.

According to some embodiments of the present invention, the amount of blowing catalyst may typically range between 0.01 and 7 pbw. The amount of gelling catalyst may typically be in the range of 0.01 to 6 pbw. A typical amount of water may range between 0.01 and 50 pbw. These pbw are to be understood as gram per 100 grams of the components of the combination of isocyanate reactive components and all other components other than the isocyanates in the reaction system, such as, as the case may be, the polyol, water, any additives such as surfactants, flame retardants, antioxidants, and amine catalysts.

According to a second aspect of the present invention a method for providing a polyurethane or polyurea foamed material is provided. The method comprises
a. Providing ingredients of a reaction mixture, said ingredients being at least
   a polyisocyanate component;
   an isocyanate-reactive component;
   water;
   a catalyst system comprising at least first catalyst suitable as a gelling catalyst in an reaction of an polyisocyanate component and an isocyanate-reactive component and a second catalyst, different from said first catalyst and suitable as a blowing catalyst in an reaction of an polyisocyanate component and an isocyanate-reactive component, said second catalyst being a component according to the formula I being $(R^1R^2NR^3)_2NR^4$ wherein
      each of $R^1$ and $R^2$ are chosen from the group consisting of a methyl group, an ethyl group, an iso-propyl group and an n-propyl group;

R³ being an alkoxyalkyl group chosen from the group consisting of —CH₂CH₂OCH₂CH₂—, —CH₂CH₂OCH₂CH₂CH₂— and —CH₂CH₂CH₂OCH₂CH₂CH₂—;

R⁴ is chosen from the group consisting of a hydrogen and —CH₂CH₂CH₂NH₂, b. Reacting said polyisocyanate component, said water and said isocyanate-reactive component in the presence of said catalyst system.

According to a further, third aspect of the present invention, a catalyst system suitable for catalyzing the reaction of said polyisocyanate component, water and a isocyanate-reactive component to provide a foamed polyurethane or polyurea material is provided. the catalyst system comprises at least a first catalyst suitable as a gelling catalyst in an reaction of an polyisocyanate component and an isocyanate-reactive component and a second catalyst, different from said first catalyst and suitable as a blowing catalyst in an reaction of an polyisocyanate component and an isocyanate-reactive component, said second catalyst being a component according to the formula I being $(R^1R^2NR^3)_2NR^4$ wherein each of $R^1$ and $R^2$ are chosen from the group consisting of a methyl group, an ethyl group, an iso-propyl group and an n-propyl group;

$R^3$ being an alkoxyalkyl group chosen from the group consisting of —CH₂CH₂OCH₂CH₂—, —CH₂CH₂OCH₂CH₂CH₂— and —CH₂CH₂CH₂OCH₂CH₂CH₂—;

$R^4$ is chosen from the group consisting of a hydrogen and —CH₂CH₂CH₂NH₂.

According to a further fourth aspect of the present invention, a primary amine is provided, which primary amine has the formula $(R^1R^2NR^3)_2NR^4$ wherein each of $R^1$ and $R^2$ are chosen from the group consisting of a methyl group, an ethyl group, an iso-propyl group and an n-propyl group;

$R^3$ being an alkoxyalkyl group chosen from the group consisting of —CH₂CH₂OCH₂CH₂—, —CH₂CH₂OCH₂CH₂CH₂— and —CH₂CH₂CH₂OCH₂CH₂CH₂—;

$R^4$ is —CH₂CH₂CH₂NH₂.

The independent and dependent claims set out particular and preferred features of the invention. Features from the dependent claims may be combined with features of the independent or other dependent claims as appropriate.

The above and other characteristics, features and advantages of the present invention will become apparent from the following detailed description which illustrates, by way of example, the principles of the invention. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

The following terms are provided solely to aid in the understanding of the invention.

A gelling catalyst is to be understood as a catalyst mainly catalyzing the reaction of isocyanate groups with alcohol groups, though sometimes also the reaction of isocyanate groups with water may be catalyzed to a minor extent.

A blowing catalyst is to be understood as a catalyst mainly catalyzing the reaction of isocyanate groups with water, though sometime also the reaction of isocyanate groups with alcohols or amines may be catalyzed to a minor extent.

Unless otherwise indicated, % w and w % of a component indicate the weight of the component over the total weight of the composition it forms part of.

The various aspects of the present invention will further be described in detail by means of one or more examples relating to the use of Bis-(N,N-2-dimethylaminoethoxyethyl)amine (also referred to as T22), Bis-(N,N-2-dimethylaminoethoxyethyl)formamide (also referred to as T22-formamide) and the reduced adduct of acrilonitrile and Bis-(N,N-2-dimethylaminoethoxyethyl)amine (also referred to as T22-ACN-reduced).

First, the provision of Bis-(N,N-2-dimethylaminoethoxyethyl)amine from a mixture further comprising N,N-dimethylbisaminoethylether (T2 MBAEE or T2), N,N,N'-trimethyl-bisaminoethylether (T3 MBAEE or T3), and/or N,N,N',N'-tetramethylbisaminoethylether (T4 MBAEE or T4) as well as the provision of Bis-(N,N-2-dimethylaminoethoxyethyl)amine and alkylated Bis-(N,N-2-dimethylaminoethoxyethyl) amin such as in particular Bis-(N,N-2-dimethylaminoethoxyethyl)methylamine, and [2-(2-{Bis-[2-(2-dimethylamino-ethoxy)-ethyl]-amino}-ethoxy)-ethyl]-dimethyl-amine will be explained.

The skilled person however understands that the same principle applies for preparation of any other secondary amines with formula $(R^1R^2NR^3)_2NH$ wherein each of $R^1$ and $R^2$ and are chosen from the group consisting of a methyl group, an ethyl group, an iso-propyl group or an n-propyl group;

$R^3$ being an alkoxyalkyl group chosen from the group consisting of —CH₂CH₂OCH₂CH₂—, —CH₂CH₂OCH₂CH₂CH₂— and —CH₂CH₂CH₂OCH₂CH₂CH₂—.

N,N-2-dimethylaminoethoxyethylamine, (also referred to as N,N-dimethylaminoethoxyethylamine, T2 or T2 MBAEE), was synthesized by reacting N,N-2-dimethyl-aminoethoxyethanol with ammonia over a copper-chromite catalyst. The reaction scheme looks like:

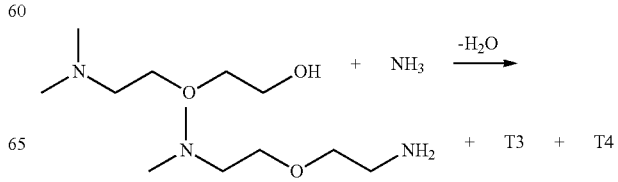

-continued

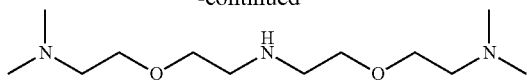

Wherein T3 refers to N,N,N'-trimethylbisaminoethylether (or T3 MBAEE) and wherein T4 refers to N,N,N',N'-tetramethylbisaminoethylether (also known as T4 MBAEE or JEFFCAT® ZF-20). N,N-2-dimethyl-aminoethoxyethanol is also known as JEFFCAT® ZR-70.

In the reactor effluent the following materials were identified:

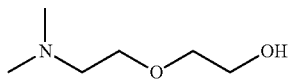

N,N-2-dimethylaminoethoxyethanol

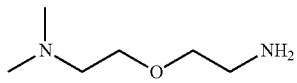

N,N-2-dimethyaminoethoxyethylamine (also referred to as T2)

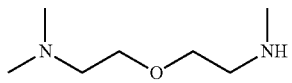

N,N,N'-trimethylbisaminoethylether (also referred to as T3) and

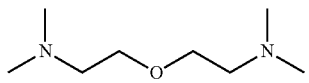

N,N,N',N'-tetramethylbisaminoethylether (also referred to as T4).

Also, a dimerized form of T2 was detected in the reactor effluent as a main component, which is:

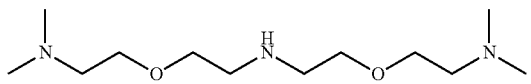

Bis-(N,N-2-dimethylaminoethoxyethyl)amine (hereinafter also referred to as "T22" or "T2-dimer"), molecular weight (hereinafter MW) 247.

Further other components were identified as various compounds structurally similar to bis-(N,N-2-dimethylaminoethoxy-ethyl)-amine, e.g. the methylated derivative of N,N-bis(2-aminoethoxyethyl-)amine, having the structure:

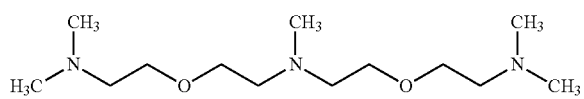

i.e. bis-(N,N-2-dimethylaminoethoxyethyl-1)methylamine (also referred to as "TM22") or by IUPAC nomenclature: 2,8,14-triaza-5,11-dioxa-2,8,14-trimethyl-pentadecane), MW 261.

Further components having a similar structure as T22 are

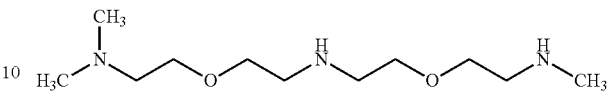

[2-(2-Dimethylamino-ethoxy)-ethyl]-[2-(2-methylamino-ethoxy)-ethyl]-amine or by IUPAC nomenclature: 2,8,14-triaza-5,11-dioxa-2-methyl-pentadecane, MW 233, and

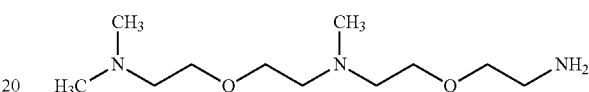

[2-(2-Amino-ethoxy)-ethyl]-[2-(2-dimethylamino-ethoxy)-ethyl]-methyl-amine or by IUPAC nomenclature: 2,8,14-triaza-5,11-dioxa-2,8-dimethyl-tetradecane; MW 233, and some minor amount of

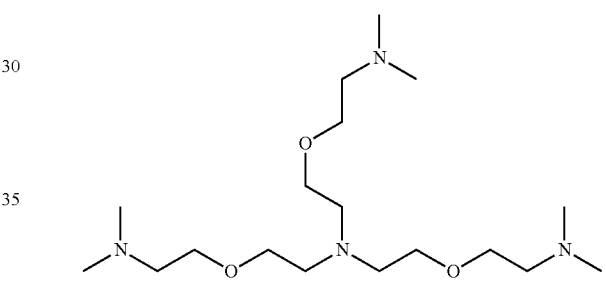

[2-(2-{Bis-[2-(2-dimethylamino-ethoxy)-ethyl]-amino}-ethoxy)-ethyl]-dimethyl-amine; MW 362.

The reactor effluent was split by distillation into three fractions:
- a light fraction, essentially consisting of water and morpholines.
- a middle fraction containing T2, T3, T4 and N,N-2-dimethylaminoethoxyethanol, and
- a heavy fraction consisting mainly of bis-(N,N-2-dimethylaminoethoxyethyl)amine and the other heavy components.

EXAMPLE 1

Provision of T2/T3/T4/T22 mixture by reacting dimethylaminoethoxyethanol with ammonia A 1000 ml stainless steel reactor was charged with 2000 g commercial $2CuOxCr_2O_3$ catalyst (CAS #99328-50-4, from Aldrich). The head of the continuous reactor system was connected with separate inlet lines and feed pumps for liquid ammonia and dimethylaminoethoxyethanol.

Ammonia and N,N-2-dimethylaminoethoxyethanol were charged to the reactor at different reaction conditions, as shown in Table 1. The reactor effluents were taken off at the bottom of the reactor, depressurized, degassed and collected for analysis and further use. All running conditions and compositions of the reactor effluents are shown in Table 1.

TABLE 1

Running conditions and product composition

| Reaction conditions | unit | Run 1 | Run 2 | Run 3 | Run 4 | Run 5 |
|---|---|---|---|---|---|---|
| Reactor temperature | °C. | 170 | 180 | 190 | 200 | 170 |
| Reactor pressure | bar | 70 | 70 | 70 | 70 | 70 |
| Catalyst load | | | | | | |
| ammonia | ltr/h | 0.1 | 0.1 | 0.1 | 0.1 | 0.1 |
| N,N-2-dimethylaminoethoxyethanol | ltr/h | 0.5 | 0.5 | 0.5 | 0.5 | 0.13 |
| Mol ratio ammonia versus N,N-2-dimethylaminoethoxyethanol | | 1.6:1 | 1.6:1 | 1.6:1 | 1.6:1 | 6:1 |

Product composition [wt.-%]

| Compound | | Run 1 | Run 2 | Run 3 | Run 4 | Run 5 |
|---|---|---|---|---|---|---|
| morpholine | [wt.-%] | 0.18 | 0.53 | 0.79 | 1.12 | 0.37 |
| N-methylmorpholine | [wt.-%] | 0.26 | 0.70 | 1.16 | 1.89 | 0.30 |
| N,N-2-dimethyl-aminoethoxyethylamine | [wt.-%] | 6.63 | 6.61 | 8.60 | 7.96 | 13.88 |
| N,N,N'-trimethylbisaminoethylether | [wt.-%] | 0.38 | 0.95 | 1.69 | 2.31 | 0.08 |
| N,N,N',N'-tetramethylbisaminoethylether | [wt.-%] | 0.52 | 1.71 | 1.80 | 2.71 | 0.40 |
| N,N-2-dimethylaminoethoxyethanol | [wt.-%] | 79.32 | 67.34 | 52.92 | 47.23 | 51.48 |
| bis-(N,N-2-dimethyl-aminoethoxyethyl)amine | [wt.-%] | 9.25 | 13.18 | 20.82 | 21.14 | 25.60 |
| compounds structurally similar to bis-(N,N-2-dimethylamino-ethoxy-ethyl)-amine | [wt.-%] | 3.64 | 8.98 | 12.22 | 15.64 | 7.12 |

All reactor effluents were combined (resulting in 8500 g crude material) and fractioned on a batch-type distillation tower, containing structured packings, having a total packing length of 100 cm. A main split was carried out to divide the combined reactor effluents in to three fractions. Fraction #1 and fraction #2 were collected as overhead products, whereas fraction #3 was taken as the residue stream.

Fraction #1 was containing all reaction water and various light boiling components like morpholine, N-methylmorpholine and others. Fraction #2 contained mainly N,N-2-dimethylaminoethoxyethylamine, N,N,N'-trimethylbisaminoethylether, N,N,N',N'-tetramethylbisaminoethylether, and N,N-2-dimethyl-aminoethoxyethanol. Working conditions and results of the main split distillation are shown in Table 2.

TABLE 2

Conditions and results of main splitting distillation forming fractions#1 and fraction#2

| | unit | fraction #1, Example 1 | fraction #2, Example 1 |
|---|---|---|---|
| Boiling range, head temperature | °C. | 48-98 | 98-133 |
| Boiling range, pot temperature | °C. | 92-143 | 143-145 |
| Pressure | mbar | 100 | 100 |
| Reflux:take off ratio (vapour divider) | | 05:01 | 15:01 |
| product composition [wt.-%] *) | | | |
| morpholine | [wt.-%] | nd | 0.43 |
| N-methylmorpholine | [wt.-%] | nd | 0.22 |
| N,N-2-dimethylaminoethoxyethylamine (=A) | [wt.-%] | nd | 40.07 |
| N,N,N'-trimethylbis-aminoethylether (=B) | [wt.-%] | nd | 11.01 |
| N,N,N',N'-tetramethylbisaminoethylether (=C) | [wt.-%] | nd | 14.70 |
| N,N-2-dimethylaminoethoxyethanol | [wt.-%] | nd | 29.51 |

TABLE 2-continued

Conditions and results of main splitting distillation forming fractions#1 and fraction#2

| | unit | fraction #1, Example 1 | fraction #2, Example 1 |
|---|---|---|---|
| bis-(N,N-2-dimethylaminoethoxyethyl)amine | [wt.-%] | nd | 0.01 |
| other components | [wt.-%] | nd | 4.05 |
| Ratio A:B:C | | nd | 40:11:15 |

\* = based on water free material
nd = not determined

The bottom fractions was retained as residue fraction #3. GC-analysis of this residue-fraction #3, showed that it consists mainly of bis-(N,N-2-dimethylaminoethoxyethyl) amine and some other components. Further examination and analysis showed that these other components are structurally similar to bis-(N,N-2-dimethylaminoethoxyethyl)amine, some being identified as

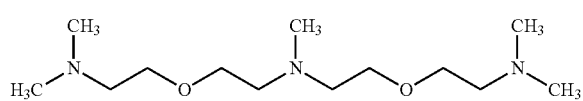

bis-(N,N-2-dimethylaminoethoxyethyl-1)methylamine (also referred to as "TM22") or by IUPAC nomenclature: 2,8,14-triaza-5,11-dioxa-2,8,14-trimethyl-pentadecane), MW 261, and

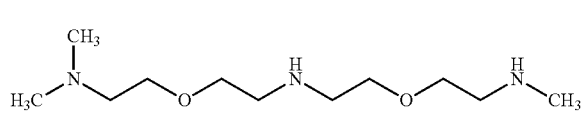

[2-(2-Dimethylamino-ethoxy)-ethyl]-[2-(2-methylamino-ethoxy)-ethyl]-amine or by IUPAC nomenclature: 2,8,14- triaza-5,11-dioxa-2-methyl-pentadecane. There are indications that another trace-impurity in T22 is

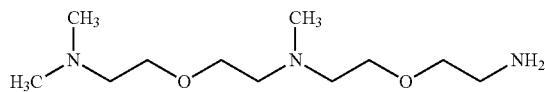

[2-(2-Amino-ethoxy)-ethyl]-[2-(2-dimethylamino-ethoxy)-ethyl]-methyl-amine or by IUPAC nomenclature: 2,8,14-triaza-5,11-dioxa-2,8-dimethyl-tetradecane; MW 233.

Also some [2-(2-{Bis-[2-(2-dimethylamino-ethoxy)-ethyl]-amino}-ethoxy)-ethyl]-dimethyl-amine was identified.

From fraction #2 containing mainly N,N-2-dimethylaminoethoxyethylamine, N,N,N'-trimethylbisaminoethylether, N,N,N',N'-tetramethylbisaminoethylether, and N,N-2-dimethyl-aminoethoxyethanol, the N,N-2-dimethylaminoethoxyethylamine can be separated by reacting the mixture with e.g. MIBK.

The separation of the product mixture was in particular obtained by using MIBK via a Schiff base formation by following reaction scheme.

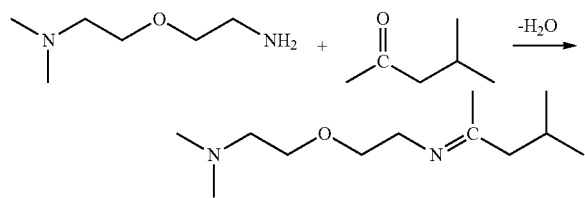

MIBK—Schiff base of T2, being {2-[2-(1,3-Dimethyl-butylideneamino)-ethoxy]-ethyl}-dimethyl-amine.

This T2-based imine has a boiling point estimated above 300° C. A boiling point of 160 to 161° C. was measured at 1 mbar vacuum.

This way, after the Schiff base is formed by dewatering, a mixture of N,N,N'-trimethylbisaminoethylether and N,N,N',N'-tetramethylbisaminoethylether is removed by vacuum distillation from the high boiling Schiff base. Thereafter, the remaining Schiff base is hydrolyzed back by a large excess of water and simultaneously removal of the formed MIBK by an azeotropic distillation. Substantially pure N,N-2-dimethylaminoethoxyethylamine is remaining in the distillation flask and optionally a subsequent fine fractionation delivers purified N,N-2-dimethylbisaminoethylether.

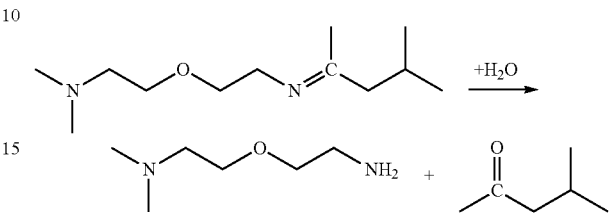

The recovered N,N-2-dimethylaminoethoxyethylamine shows after distillation a purity of 99+ wt.-%, whereas the N,N,N'-trimethylbisaminoethylether/N,N,N',N'-tetramethylbisaminoethylether mixture was substantially free of N,N-2-dimethylaminoethoxyethylamine.

For Schiff base reaction, MIBK (methylisobutylketone) can be replaced by various other carbonyl compounds. Other carbonyl compounds are e.g. cyclohexanone, isovaleraldehyde and alike. In case of MIBK, no azeotropic entraining agent is necessary, because MIBK acts as both as reagent for the Schiff base formation and as entraining agent as well. If other carbonyl compounds are chosen usually suitable entraining solvents are needed, preferably being hydrocarbons, such as methylcyclohexane, toluene or xylene or a xylene isomer blend.

The bottom fractions which was retained as residue fraction #3, this heavy fraction could be recovered as follows:

The heavy fraction was distilled at different vacuum- and temperature conditions on a batch-type distillation tower, containing structured packing, having a total packing length of 100 cm. After a short transition fraction, fraction #4, two product fractions, fraction #5 and fraction #6 were taken.

Working conditions and results of distillation of residue-fraction #3 are shown in Table 3.

TABLE 3

| conditions and results of distillation of residue-fraction#3 | | | | |
|---|---|---|---|---|
| | unit | Example 1, fraction #4 | Example 1, fraction #5 | Example 1, fraction #6 |
| Boiling range, head temperature | ° C. | 20-20 | 120-125 | 125-128 |
| Boiling range, pot temperature | ° C. | 20-120 | 169-174 | 174-175 |
| Pressure | mbar | 7 | 7 | 7 |
| Reflux:take off ratio (vapour divider) | | 2:1 | 2:1 | 2:1 |
| product composition [wt.-%] *) | [wt.-%] | Example 1, fraction #4 | Example 1, fraction #5 | Example 1, fraction #6 |
| morpholine | [wt.-%] | nd | 0 | 0 |
| N-methylmorpholine | [wt.-%] | nd | 0 | 0 |
| N,N-2-dimethylaminoethoxyethylamine (= A) | [wt.-%] | nd | 0 | 0 |
| N,N,N'-trimethylbis-aminoethylether (= B) | [wt.-%] | nd | 0 | 0 |
| N,N,N',N'-tetramethylbisaminoethylether (= C) | [wt.-%] | nd | 0 | 0 |
| N,N-2-dimethylaminoethoxyethanol | [wt.-%] | nd | 0.17 | 0.01 |

TABLE 3-continued

| conditions and results of distillation of residue-fraction#3 | | | | |
|---|---|---|---|---|
| bis-(N,N-2-dimethylaminoethoxyethyl)amine | [wt.-%] | nd | 83.83 | 81.02 |
| compounds structurally similar to bis-(N,N-2-dimethylamino-ethoxy-ethyl)-amine | [wt.-%] | nd | 16.0 | 18.97 |

\* = based on water free material
nd = not determined 868 g of fraction #5/Example 1 was filled in to a 2 liter distillation flask of a batch type distillation tower containing structured packings (packing length=1 m).

A careful fractionation resulted 470.2 g of a product (fine fraction #2 in table 4) containing 87.7 wt.-% bis-(N,N-2-dimethyl-aminoethoxyethyl)amine ("T22"). Conditions and results are shown in Table 4.

TABLE 4

Conditions and results of fine fractionation of fraction#5/Example 1

| | unit | Fine fraction #1, | Fine fraction #2, |
|---|---|---|---|
| Boiling range, head temperature | ° C. | 150-151 | 151-152 |
| Boiling range, pot temperature | ° C. | 173-174 | 174 |
| Pressure | mbar | 7 | 7 |
| Reflux:take off ratio (vapour divider) | | 20:01 | 20:01 |

| product composition [wt.-%] *) | [wt.-%] | Fine fraction #1, | Fine fraction #2, |
|---|---|---|---|
| N,N-2-dimethylaminoethoxyethanol | [wt.-%] | nd | 0 |
| bis-(N,N-2-dimethylaminoethoxyethyl)amine | [wt.-%] | nd | 87.73 |
| bis-(N,N-2-dimethylaminoethoxyethyl)methylamine | [wt.-%] | nd | 8.81 |
| [2-(2-Amino-ethoxy)-ethyl]-[2-(2-dimethylamino-ethoxy)-ethyl]-methyl-amine | [wt.-%] | nd | 3.46 |

\* = based on water free material
nd = not determined

The structure of bis-(N,N-2-dimethyl-aminoethoxyethyl)amine was verified by GC/MS spectroscopy. The other components were identified as structural isomer of bis-(N,N-2-dimethylamino-ethoxy-ethyl)-amine or compounds structurally similar to bis-(N,N-2-dimethylamino-ethoxy-ethyl)-amine.

A boiling point of 300° C. is estimated for bis-(N,N-2-dimethylamino-ethoxy-ethyl)-amine. A boiling point of 150-152° C. at 7 mbar vacuum is measured To separate and refine T22 from this mixture, the fractions #5 and/or #6 of example 1 were reacted with formic acid.

TM22 could not react with the formic acid

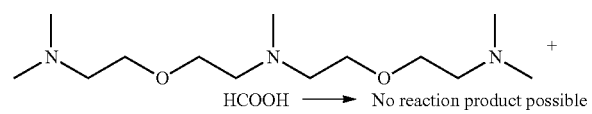

HCOOH → No reaction product possible

Following reactions occurred:

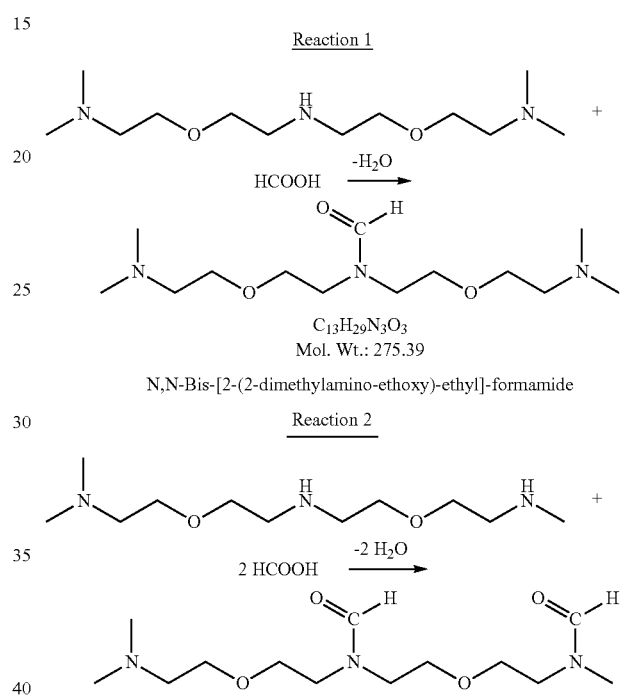

It can be easily seen from these reactions, that TM22 does not form any formylation product. T22 is provided by such a formylation reaction and by addition of one formyl group a mono formamide, namely N,N-Bis-[2-(2-dimethylamino-ethoxy)-ethyl]-formamide (reaction 1), whereas the formylation reaction shown by reaction 2 is resulting a product having two formyl groups in the molecule. A result of this measure is a large differentiation of the boiling points of TM22 and the formed formamides. By a simple vacuum distillation, optionally even without utilizing a fractionation tower, TM22 appears as a "light end component". The N,N-bis-[2-(2-dimethylamino-ethoxy)-ethyl]-formamide is forming the main fraction, having a purity of 98% or more (the remainder being impurities due to the reaction steps as described above), whereas the other formamide as shown in reaction 2 is remaining in the distillation residue due to the difference of its boiling point with the N,N-Bis-[2-(2-dimethylamino-ethoxy)-ethyl]-formamide.

Subsequent deformylation of the N,N-bis-[2-(2-dimethylamino-ethoxy)-ethyl]-formamide provides T22 in good yield and appreciable purity. Such a deformylation reaction can be carried out under acidic or alkalinic reaction condition. In the following reaction 3 alkalinic conditions were chosen using e.g. potassium hydroxide.

Reaction 3

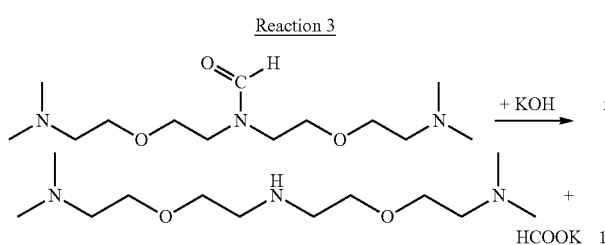

The fraction 5 was further refined and bis-(N,N-2-dimethyl-aminoethoxyethyl)amine was separated from the other bis-(N,N-2-dimethyl-aminoethoxyethyl)amine isomers, by distillation. To remove the light fraction, the temperature of the mixture in the reactor may be chosen in the range of 173-175° C., the temperature of the head of the column may be chosen in the range of 150-151° C. The pressure can be 7 mbar. To remove the middle fraction, the temperature of the mixture in the reactor may be chosen in the range of 174-175° C., the temperature of the head of the column may be chosen in the range of 151-152° C. The pressure may be 7 mbar. The column may comprise of 15-30 trays of structured packing.

Substantially pure bis-(N,N-2-dimethyl-aminoethoxyethyl)amine was obtained, i.e. bis-(N,N-2-dimethyl-aminoethoxyethyl)amine with a purity of 87 w %. Remaining compounds are bis-(N,N-2-dimethylaminoethoxyethyl-1) methylamine (also referred to as "TM22") or by IUPAC nomenclature: 2,8,14-triaza-5,11-dioxa-2,8,14-trimethyl-pentadecane), MW 261 (0.1-18 w %) and [2-(2-Dimethylamino-ethoxy)-ethyl]-[2-(2-methylamino-ethoxy)-ethyl]-amine or by IUPAC nomenclature: 2,8,14-triaza-5,11-dioxa-2-methyl-pentadecane (0.1-18 w %) and [2-(2-Aminoethoxy)-ethyl]-[2-(2-dimethylamino-ethoxy)-ethyl]-methyl-amine or by IUPAC nomenclature: 2,8,14-triaza-5,11-dioxa-2,8-dimethyl-tetradecane; MW 233 (0.1-18 w %). Some other unknown high boiling components may be present.

To provide the reduced adduct of N,N-Bis-[2-(2-dimethylamino-ethoxy)-ethyl]-amine and acrylonitrile, following multiple step process was applied.

a Cyanoethylation of bis-(N,N-2-dimethylaminoethoxyethyl)amine 400 g of "crude T22" bis-(N,N-2-dimethylaminoethoxyethyl)amine were recycled through a reactor column of 27 mm inner diameter, 80 cm length, filled with 200 ml of Amberlyst® A26 (Rohm & Haas, via Aldrich). Over a total period 24 hours were 71 g of acrylonitrile added to the recycle stream. During this cyanoethylation step the reaction temperature was kept at 50° C. After the end of the reaction period the reaction mixture was carefully filtered and used for the subsequent nitrile hydrogenation step.

b Nitrile hydrogenation of the cyanoethylated bis-(N,N-2-dimethylaminoethoxyethyl)amine.

The cyanoethylated bis-(N,N-2-dimethylaminoethoxyethyl)amine of step a-) was hydrogenated over a Raney® 2786 catalyst (Grace Corp., available from Aldrich) placed in a 100 ml reactor at 70 bar and 120° C. The hydrogenation feedstock was sent over the catalyst bed by a total chargetime of 24 hours and aprox. 10 g ventgas/liquid*hours.

Apart of some losses by washing the catalyst bed all hydrogenated material was collected for further working up.

c Distillation of hydrogenated nitrile 400 g hydrogenated reactor effluent were transferred in to a Büchi-Rotavapor® apparatus an subsequently flash-distilled. After a small fore-cut, taken up to 80° C. head temperature at a pressure of 100 mbar, the bulk of material was distilled at 1 mbar up to 180° C. head temperature. In total were 340 g distillate collected. The flash-distillate was fractionated on a batch-type distillation tower, containing structured packings (Sulzer® EX), having a total packing length of 100 cm. Working conditions and results of this distillation are shown in Table 5.

TABLE 5

Purification of N,N-bis-[2-(2-dimethylaminoethoxy)ethyl]propanane-1,3-diamine

| | unit | Example 7 fraction #1 | Example 7 fraction #2 | Example 7 fraction #3 |
|---|---|---|---|---|
| Boiling range, head temperature | ° C. | 166-170 | 170 | 170 |
| Boiling range, pot temperature | ° C. | 20-215 | 215-264 | 264-268 |
| Pressure | mbar | 2 | 2 | 2 |
| Reflux:take off ratio (vapour divider) | | 10:1 | 10:1 | 10:1 |

| product composition [wt.-%]* | [wt.-%] | Example 7 fraction #1 | Example 7 fraction #2 | Example 7 fraction #3 |
|---|---|---|---|---|
| N,N-bis-[2-(2-dimethylaminoethoxy)ethyl]-propanane-1,3-diamine | [wt.-%] | nd | 97.19 | 97.19 |
| Σ unknowns | [wt.-%] | nd | 2.81 | 2.81 | nd = not determined

The fractions #2 and #3 combined, straight after the end of the distillation resulting 250 g product in total. This material was investigated by GC analysis and GC/MS spectroscopy. The product was identified by GC/MS spectroscopy to be N,N-bis-[2-(2-dimethylaminoethoxy)ethyl]propanane-1,3-diamine and is therewith in conformity with the structure:

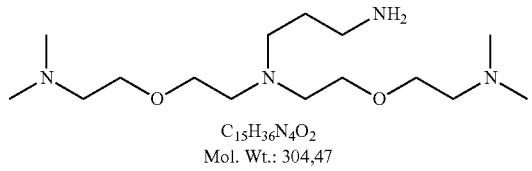

$C_{15}H_{36}N_4O_2$
Mol. Wt.: 304,47

N,N-bis-[2-(2-dimethylaminoethoxy)ethyl]propanane-1,3-diamine

The purity of the product was found to be 97.19 wt.-% by GC. The estimated atmospheric boiling point is expected to be between 380 and 450° C., the liquid density at 20° C. was determined as 0.94 g/ml.

Following different components were used as a blowing catalyst component of a catalyst system in the production of flexible polyurethane foam:

A* Jeffcat ® ZF-22 = bis-(2-dimethylaminoethyl)ether at 70% w in dipropyleneglycol
B  T2 = N,N-dimethylbisaminoethylether
C  T22 = N,N-Bis-[2-(2-dimethylamino-ethoxy)-ethyl]-amine
D* TM22 = N,N-Bis-[2-(2-dimethylamino-ethoxy)-ethyl]-methyl-amine
E* T22-formamide = N,N-Bis-[2-(2-dimethylamino-ethoxy)-ethyl]-formamide -continued

| | |
|---|---|
| F | T22-ACN-adduct reduced = N,N-Bis-[2-(2-dimethylamino-ethoxy)-ethyl]-N-3-aminopropylamine, also referred to as [2-(2-{[2-(2-aminoethoxy)ethyl](3-aminopropyl)amino}ethoxy)ethyl]dimethylam |

*are comparative catalyst components

Component B is a component corresponding to Formula. $(R^1R^2NR^3)NH_2$.

Components C, and F are components according to the formula I, i.e. $(R^1R^2NR^3)_2NR^4$ In all formulae, each of $R^1$ and $R^2$ are a methyl groups;

$R^3$ are —$CH_2CH_2OCH_2CH_2$—;

$R^4$ is a hydrogen (component C),

—$CH_2CH_2CH_2NH_2$ (component F)

In the formulations, Jeffcat® DPA was used as the gelling catalyst component, being N-(3-dimethylaminopropyl)-N,N-diisopropanolamine The amount of blowing catalyst was defined for each of the components A to G, for providing a flexible foam with comparable Cream-, Top of Cup and Gelation times, in order to obtain comparable foam systems. Following formulations were compared:

Formulations:

| | fA* | fB | fC1 | fD* | fE* | fF | fC2 |
|---|---|---|---|---|---|---|---|
| JEFFOL ® G31-28 | 60.00 | 60.00 | 60.00 | 60.00 | 60.00 | 60.00 | 60.00 |
| JEFFOL ® PPG-3706 | 40.00 | 40.00 | 40.00 | 40.00 | 40.00 | 40.00 | 40.00 |
| TEGOSTAB ® B 8734 LF2 | 0.60 | 0.60 | 0.60 | 0.60 | 0.60 | 0.60 | 0.60 |
| Diethanolamine, 85% Low Freeze Grade | 1.00 | 1.00 | 1.00 | 1.00 | 1.00 | 1.00 | 1.00 |
| Deionized Water | 3.85 | 3.85 | 3.85 | 3.85 | 3.85 | 3.85 | 3.85 |
| A: JEFFCAT ® ZF-22 Amine Catalyst | 0.10 | | | | | | |
| B: T2 | | 0.60 | | | | | |
| C: T22 | | | 0.53 | | | | |
| D: TM22 | | | | 0.15 | | | |
| E: T22-Formamide | | | | | 0.72 | | |
| F: T22-ACN-Adduct (Reduced) | | | | | | 0.36 | |
| C: T22 | | | | | | | 0.53 |
| JEFFCAT ® DPA Amine Catalyst | 1.13 | 1.13 | 1.13 | 1.13 | 1.13 | 1.13 | 1.13 |
| Formula Weight | 106.68 | 107.18 | 107.11 | 106.73 | 107.30 | 106.94 | 107.11 |
| Isocyanate Index | 90 | 90 | 90 | 90 | 90 | 90 | 90 |
| SUPRASEC ® 7320 | 67.4 | 68.6 | 67.7 | 67.5 | 67.9 | 67.6 | 67.7 |

*formulations fA, fD and fE are comparative formulations
all amounts of the various components are expressed by weight parts The component C (T22) used in fC1 comprises 88.7% w of T22, 9.2 w % of TM22 and 2.1% of other components.

The component C (T22) used in fC2 comprises 87.7% w of T22, 8.8 w % of TM22 and 3.5% of other components.

Jeffol® G31-28 of Huntsman International LLC is an EO tipped, dipropyleneglycol initiated PO-diol with Molecular weight of about 3800.

Jeffol® PPG-3706 of Huntsman International LLC is an EO tipped, glycerine initiated PO-triol with Molecular weight of about 6000

Tegostab® B 8734 LF2 is a silicone surfactant of Evonic.

SUPRASEC® 7320 of Huntsman International LLC is an MDI-based polyisocyanate being a mixture of polymeric MDI, an MDI prepolymer and an MDI isomer mixture.

A blend of the components set out above, except the polyisocyanate component, was made, containing the catalyst use level as set out in the table above. The blend was mixed for 5 minutes at 900 RPMs using the RYOBI® 10" Drill Press with EXACTLINE™ Laser System. To produce foam in an open box, 250 grams of the blend was poured into a Solo® 64 ounce lined paper cup and mixed with a 2 inch ITC Style Conn Blade® for 24 seconds and at 3050 RPMs, using the RYOBI® 10" Drill Press with EXACTLINE™ Laser System. A calculated amount of SUPRASEC® 7320 Isocyanate (Huntsman Corporation) was added and mixed for 6 seconds. At the end of 6 seconds, the contents were poured into a 12 inch by 6 inch by 6 inch open box and the foam was allowed to rise until completion was made.

The foam bun was allowed to cure for 30 minutes and after curing, three foam samples were extracted, using a Feather® No. 11 Disposable Scalpel, from three different areas and placed into three labeled 4 dram GC vials. Three 2 inch by 2 inch by 1 inch foam blocks were cut from three different areas, using the CRAFTSMAN® Professional 18 inch 4 Speed Metal/Wood Cutting Band Saw, and were analyzed for air flow and density. To determine the air flow, the Gulbrandsen Foam Porosity Measurement Instrument was turned on and the foam block was inserted. The high air flow valve was opened until the pressure read 125 kilopascals and the air flow reading was recorded in standard cubic feet per minute. To determine the density, the volume of the foam block was calculated and the weight of the foam sample was determine and using these two values, the density was calculated into pounds per cubic feet.

The Daimler thermal desorption analysis method PB VWL 709 which has both a VOC and a FOG component to the resultant data report was used to specify the VOC and FOG properties of the foams obtained. In this quantitative and dynamic headspace type test, VOC emissions are measured from a very small foam sample that is placed in a thermal desorption tube and continually flushed with an inert gas for thirty minutes at 90° C. The volatiles carried away by the flush gas are collected in a −150° C. cryogenic trap and later reheated and conveyed into a GC/MS instrument for further analysis and calculation of total VOC (volatile organic chemicals) expressed in parts per million (ppm). In the FOG portion of the test, the same sample is heated to 120° C. and is swept by the carrier gas for an additional one hour. Volatiles collected in the cryogenic trap are then analyzed by the GC/MS instrumentation to obtain the final FOG results.

Following results were obtained

| formulation | Cream time (sec) | Top of cup time (sec) | Gelation time (sec) | Air flow (scfm) | Free rise density (pcf) |
|---|---|---|---|---|---|
| fA* | 7 | 39 | 58 | 3.1 | 2.21 |
| fB | 7 | 40 | 55 | 3.4 | 1.93 |
| fC1 | 7 | 40 | 55 | 3.2 | 2.14 |
| fC2 | 8 | 39 | 56 | 3.1 | 2.13 |
| fD* | 7 | 38 | 55 | 2.9 | 2.9 |
| fE* | 7 | 39 | 54 | 3.1 | 3.1 |
| fF | 7 | 39 | 58 | 2.9 | 2.9 |

*are comparative formulations

In the VOC and FOG test, the components emitted were characterized and quantified as follows

| | | | VOC | | | | |
|---|---|---|---|---|---|---|---|
| Component (ppm) | fA* | fB | fC1 | fC2 | fD* | fE* | fF |
| A | 137.6 | 0 | 0 | 0 | 0 | 0 | 0 |
| B | 0 | 0 | 0 | 0 | 0 | 0 | 0 |
| C | 0 | 0 | 0 | 0 | 0 | 0 | 0 |
| D | 0 | 0 | 19.8 | 38.4 | 71.95 | 0 | 0 |
| E | 0 | 0 | 0 | 0 | 0 | 0 | 0 |
| F | 0 | 0 | 0 | 0 | 0 | 0 | 0 |
| DPA | 0 | 0 | 0 | 0 | 0 | 0 | 0 |
| Total VOC | 219.9 | 55.2 | 102.19 | 61.22 | 148.35 | 79.22 | 51.88 |

| | | | FOG | | | | |
|---|---|---|---|---|---|---|---|
| Component (ppm) | fA* | fB | fC1 | fC2 | fD* | fE* | fF |
| A | 0 | 0 | 0 | 0 | 0 | 0 | 0 |
| B | 0 | 0 | 0 | 0 | 0 | 0 | 0 |
| C | 0 | 0 | 0 | 0 | 0 | 0 | 0 |
| D | 0 | 0 | 29.4 | 38.4 | 125.45 | 0 | 0 |
| E | 0 | 0 | 0 | 0 | 0 | 719.1 | 0 |
| F | 0 | 0 | 0 | 0 | 0 | 0 | 0 |
| DPA | 0 | 0 | 0 | 0 | 0 | 0 | 0 |
| Total FOG | 120.7 | 79.95 | 139.8 | 168.35 | 281.85 | 843.95 | 125.8 |

As is clear from the figures above, the components T2, T22 and T22-ACN-adduct reduced does not show in the VOC and FOG tests. JEFFCAT® ZF-22 (fA) and TM22, either used as such (fD) of as a contaminant in the T22 (fC1 and fC2) contributes to VOC, and TM22 shows up in the FOG tests.

Thence using pure T22, comprising only about 0.1% w of TM22, will have a lower score rate at the total VOC and total FOG.

Also the component T22-formamide (fE) does not show up on the VOC tests, but does contribute in the FOG test.

Other polyurethane foams were made as follows:

1728 grams of a master batch solution composed of 100 parts of VARNOL 3136 (Dow chemical Co), 2.8 parts of deionized water, 1.0 parts of SURFONIC L-620 (Momentive Performance Materials), and JEFFCAT® TD-33a catalysts, 0.3 parts were thoroughly mixed together for 1 hour on a roller mixer. This polyol mixture, 249.84 grams, was added to a 1.8 liter paper cup. The correct amount of blowing catalysts, as indicated in the table below, was added to the cup. The mixture was then mixed at 2500 RPM for 7 seconds. Kosmos 15P, 0.72 ml (Evonik Goldschmidt) is added to the mixture and mixed with the 2500 RPM stirrer for seven seconds. Mondur TD-80, toluendediidocyanate (TDI) (Bayer), 93.89 grams is added and an additional seven seconds of mixing this mixture, using the 2500 RPM mixer, is completed. This mixture is then poured into a Cardboard box having a dimension of 30.4 by 15.2 by 15.2 cm. The cream time is noted. The time for the foam to rise above the top of the box is noted. The blow off time is also noted. After the foam is cured, three 5.1 by 5.1 by 2.54 cm foam blocks are cut from the center of the foam block. Air flow measurements are completed on these samples and averaged. The airflow data is also shown in the table.

EXAMPLES 1-7

Flexible Slab Foams Made with JEFFCAT TD-33a Gel Catalysts

| | fH* | fI | fJ | fK | fL* | fM* | fN |
|---|---|---|---|---|---|---|---|
| Voranol 3136 | 240 | 240 | 240 | 240 | 240 | 240 | 240 |
| Water | 6.72 | 6.72 | 6.72 | 6.72 | 6.72 | 6.72 | 6.72 |
| Niax L-620 | 2.4 | 2.4 | 2.4 | 2.4 | 2.4 | 2.4 | 2.4 |
| JEFFCAT ®TD-33A catalyst | 0.72 | 0.72 | 0.72 | 0.72 | 0.72 | 0.72 | 0.72 |
| Total Masterbatch | 249.84 | 249.84 | 249.84 | 249.84 | 249.84 | 249.84 | 249.84 |
| JEFFCAT ®ZF-22 catalyst | 0.24 | | | | | | |
| T2- | | 1.32 | | | | | |
| T22- | | | 1.06 | | | | |
| T22 crude- | | | | 1.06 | | | |
| TM22- | | | | | 0.34 | | |
| T22-formamide- | | | | | | 1.06 | |
| T22-ACN-adduct (reduced)- | | | | | | | 0.79 |
| Kosmos 15p | 0.84 | 0.84 | 0.84 | 0.84 | 0.84 | 0.84 | 0.84 |
| Index | 110 | 110 | 110 | 110 | 110 | 110 | 110 |
| Mondur TD-80 TDI | 93.88 | 93.88 | 93.88 | 93.88 | 93.88 | 93.88 | 93.88 |
| Properties of the foam | | | | | | | |
| Rise profile (times in seconds) | | | | | | | |
| CREAM TIME | 9 | 9 | 9 | 9 | 9 | 9 | 9 |
| TOP OF CUP | 39 | 42 | 43 | 43 | 38 | 46 | 42 |

-continued

|  | fH* | fI | fJ | fK | fL* | fM* | fN |
|---|---|---|---|---|---|---|---|
| BLOWOFF TIME | 99 | 102 | 103 | 103 | 96 | 103 | 102 |
| Air flow, liters/min | 90.6 | 53.8 | 62.3 | 68.0 | 84.9 | 90.6 | 68.0 |
| DENSITY g/in$^3$ | 34.60 | 33.48 | 34.76 | 33.48 | 35.08 | 33.80 | 33.80 |

*formulations fH, fL and fM are comparative formulations
all amounts of the various components are expressed by weight parts

EXAMPLES 8-14

Flexible Slab Foams Made with JEFFCAT DPA Gel Catalysts

|  | fO* | P | Q | fR | fS* | fT* | fU |
|---|---|---|---|---|---|---|---|
| Voranol 3136 | 240 | 240 | 240 | 240 | 240 | 240 | 240 |
| Water | 6.72 | 6.72 | 6.72 | 6.72 | 6.72 | 6.72 | 6.72 |
| Niax L-620 | 2.4 | 2.4 | 2.4 | 2.4 | 2.4 | 2.4 | 2.4 |
| JEFFCAT ® DPA catalyst | 0.72 | 0.72 | 0.72 | 0.72 | 0.72 | 0.72 | 0.72 |
| Total Masterbatch | 249.84 | 249.84 | 249.84 | 249.84 | 249.84 | 249.84 | 249.84 |
| JEFFCAT ® ZF-22 catalyst | 0.24 |  |  |  |  |  |  |
| T2- |  | 1.32 |  |  |  |  |  |
| T22- |  |  | 1.06 |  |  |  |  |
| T22 crude- |  |  |  | 1.06 |  |  |  |
| TM22- |  |  |  |  | 0.53 |  |  |
| T22-formamide- |  |  |  |  |  | 1.2 |  |
| T22-CAN-adduct (reduced)- |  |  |  |  |  |  | 0.79 |
| Kosmos 15p | 0.84 | 0.84 | 0.84 | 0.84 | 0.84 | 0.84 | 0.84 |
| Index | 110 | 110 | 110 | 110 | 110 | 110 | 110 |
| Mondur TD-80 TDI (Formulation Factor × 0.9) | 93.88 | 93.88 | 93.88 | 93.88 | 93.88 | 93.88 | 93.88 |
| Rise profile (time in seconds) |  |  |  |  |  |  |  |
| CREAM TIME | 9 | 10 | 9 | 9 | 9 | 9 | 8 |
| TOP OF CUP | 41 | 42 | 45 | 42 | 39 | 42 | 38 |
| BLOWOFF TIME | 101 | 99 | 105 | 103 | 101 | 101 | 96 |
| Air flow, liters/min | 118.9 | 96.3 | 113.3 | 107.6 | 118.9 | 101.9 | 56.6 |
| DENSITY g/in$^3$ | 34.44 | 35.72 | 33.16 | 33.00 | 33.80 | 33.32 | 36.36 |

*formulations fO, fS and fT are comparative formulations
all amounts of the various components are expressed by weight parts It is to be understood that although preferred embodiments and/or materials have been discussed for providing embodiments according to the present invention, various modifications or changes may be made without departing from the scope and spirit of this invention.

The invention claimed is:

1. A catalyst system suitable for catalyzing the reaction of a polyisocyanate component, water and an isocyanate-reactive component to provide a foamed polyurethane or polyurea material, said catalyst system comprising at least a first catalyst suitable as a gelling catalyst in a reaction of a polyisocyanate component and an isocyanate-reactive component and a second catalyst, different from said first catalyst and suitable as a blowing catalyst in a reaction of a polyisocyanate component and an isocyanate-reactive component, said second catalyst being a component according to formula I, formula I being $(R^1R^2NR^3)_2NR^4$, wherein
   each of $R^1$ and $R^2$ are chosen from the group consisting of a methyl group, an ethyl group, an iso-propyl group and an n-propyl group;
   $R^3$ is an alkoxyalkyl group chosen from the group consisting of —CH$_2$CH$_2$OCH$_2$CH$_2$—, —CH$_2$CH$_2$OCH$_2$CH$_2$CH$_2$—, and —CH$_2$CH$_2$CH$_2$OCH$_2$CH$_2$CH$_2$—; and
   $R^4$ is chosen from the group consisting of hydrogen and —CH$_2$CH$_2$CH$_2$NH$_2$.

2. A primary amine corresponding to formula I, formula I being $(R^1R^2NR^3)_2NR^4$ wherein
   each of $R^1$ and $R^2$ are chosen from the group consisting of a methyl group, an ethyl group, an iso-propyl group and an n-propyl group;
   $R^3$ is an alkoxyalkyl group chosen from the group consisting of —CH$_2$CH$_2$OCH$_2$CH$_2$—, —CH$_2$CH$_2$OCH$_2$CH$_2$CH$_2$—, and —CH$_2$CH$_2$CH$_2$OCH$_2$CH$_2$CH$_2$—; and
   $R^4$ is —CH$_2$CH$_2$CH$_2$NH$_2$.

3. The system according to claim 1, wherein $R^4$ is hydrogen.

4. The system according to claim 3, wherein $R^1$ and $R^2$ are methyl groups.

5. The system according to claim 1, wherein $R^4$ is —CH$_2$CH$_2$CH$_2$NH$_2$.

6. The system according to claim 1, wherein
   each of $R^1$ and $R^2$ are a methyl group;
   $R^3$ is —CH$_2$CH$_2$OCH$_2$CH$_2$—; and
   $R^4$ is hydrogen.

* * * * *